(12) United States Patent
Cavanagh et al.

(10) Patent No.: US 11,160,664 B2
(45) Date of Patent: Nov. 2, 2021

(54) DEVICES AND METHODS FOR METATARSOPHALANGEAL ARTHROPLASTY PROCEDURES

(71) Applicant: University of Washington, Seattle, WA (US)

(72) Inventors: Peter R. Cavanagh, Seattle, WA (US); Scott Telfer, Seattle, WA (US)

(73) Assignee: University of Washington, Seattle, WA (US)

( * ) Notice: Subject to any disclaimer, the term of this patent is extended or adjusted under 35 U.S.C. 154(b) by 118 days.

(21) Appl. No.: 16/633,141

(22) PCT Filed: Jul. 25, 2017

(86) PCT No.: PCT/US2017/043639
§ 371 (c)(1),
(2) Date: Jan. 22, 2020

(87) PCT Pub. No.: WO2019/022712
PCT Pub. Date: Jan. 31, 2019

(65) Prior Publication Data
US 2020/0197188 A1    Jun. 25, 2020

(51) Int. Cl.
*A61F 2/42*    (2006.01)
*A61F 2/46*    (2006.01)
(Continued)

(52) U.S. Cl.
CPC .......... *A61F 2/4225* (2013.01); *A61F 2/4606* (2013.01); *A61B 17/1775* (2016.11);
(Continued)

(58) Field of Classification Search
CPC ............ A61F 2/4225; A61F 2002/4228; A61F 2002/4233; A61F 2002/4238;
(Continued)

(56) References Cited

U.S. PATENT DOCUMENTS 4,156,296 A    5/1979   Johnson et al.
4,787,908 A    11/1988  Wyss et al.
(Continued)

FOREIGN PATENT DOCUMENTS

EP     1897509 A1      3/2008
WO     2016115172 A1   7/2016

OTHER PUBLICATIONS

Bartak V, et al., "ToeFit—Plus system for replacement of the first metatarsophalangeal joint." Acta Chir Orthop Traumatol Cech 2010; 77(3):222-227.
(Continued)

*Primary Examiner* — Javier G Blanco
(74) *Attorney, Agent, or Firm* — Perkins Coie LLP

(57) ABSTRACT

A device for use during an arthroplasty procedure of a joint of a patient, the joint extending between a first joint end of a first bone and an abutting second joint end of a second bone of the patient. The device includes first and second components that can be mated together. The first component includes an attachment fitting configured for disposing over the first joint end of the first bone and a stem extending from the attachment fitting and suitable for extending along an intra-medullary canal of the first bone. The second component includes an end plate configured to mate with the attachment fitting and a longitudinal plate extending from the end plate and configured for disposing along a medial, longitudinal surface of the first bone. The device also includes at least one fastener for coupling the longitudinal plate to the first bone.

8 Claims, 10 Drawing Sheets

(51) Int. Cl.
  *A61B 17/17* (2006.01)
  *A61B 17/72* (2006.01)
  *A61F 2/30* (2006.01)
(52) U.S. Cl.
  CPC ......... *A61B 17/7291* (2013.01); *A61F 2/4241* (2013.01); *A61F 2002/30578* (2013.01); *A61F 2002/30878* (2013.01); *A61F 2002/4233* (2013.01)
(58) Field of Classification Search
  CPC ............ A61F 2/4606; A61F 2002/4251; A61F 2/4241; A61B 17/7291
  See application file for complete search history.

(56) References Cited

U.S. PATENT DOCUMENTS

| | | | |
|---|---|---|---|
| 5,443,516 A * | 8/1995 | Albrektsson | A61F 2/3845 623/23.39 |
| 7,291,175 B1 | 11/2007 | Gordon | |
| 7,491,220 B2 | 2/2009 | Coughln | |
| 8,162,996 B2 | 4/2012 | Schelling | |
| 8,167,918 B2 | 5/2012 | Strnad et al. | |
| 8,292,966 B2 | 10/2012 | Morton | |
| 8,303,666 B2 | 11/2012 | Vanasse | |
| 2005/0085819 A1 | 4/2005 | Ellis et al. | |
| 2006/0241608 A1 | 10/2006 | Myerson et al. | |
| 2007/0299533 A1 | 12/2007 | Reiley | |
| 2008/0051912 A1 | 2/2008 | Hollawell | |
| 2008/0195215 A1 | 8/2008 | Morton et al. | |
| 2011/0066250 A1* | 3/2011 | Palmer | A61F 2/4261 623/21.12 |
| 2011/0087334 A1 | 4/2011 | Morton et al. | |
| 2011/0093084 A1 | 4/2011 | Morton et al. | |
| 2011/0093085 A1 | 4/2011 | Morton et al. | |
| 2011/0184527 A1* | 7/2011 | Vanasse | A61F 2/42 623/21.15 |
| 2012/0065689 A1 | 3/2012 | Prasad et al. | |
| 2012/0109322 A1 | 5/2012 | Gonzalez-Hernandez et al. | |
| 2013/0172942 A1 | 7/2013 | Lewis et al. | |
| 2013/0197655 A1* | 8/2013 | Scheker | A61F 2/4241 623/21.16 |
| 2014/0121779 A1 | 5/2014 | Gonzalez-hernandez | |
| 2014/0316530 A1 | 10/2014 | Early et al. | |

OTHER PUBLICATIONS

Brewster M., "Does total joint replacement or arthrodesis of the first metatarsophalangeal joint yield better functional results? A systematic review of the literature." J Foot Ankle Surg., 2010; 49(6): 546-552.

D'Angelantonio AM, et al., "Master techniques in digital arthrodesis." Clinics in Podiatric Medicine And Surgery, 2012;29(1):21-40.

Giza E, et al., "First metatarsophalangeal hemiarthroplasty for hallux rigidus." Int Orthop, 2010;34(8):1193-1198.

Hromádka R, et al., "MEDIN implant of the first metatarsophalangeal joint." Acta Chir Orthop Traumatol Cech 2012;79(2):124-130.

International Search Report and Written Opinion in International Application No. PCT/US17/43639, dated Oct. 6, 2017, 8 pages.

International Search Report and Written Opinion dated Mar. 10, 2016 in PCT/US2016/013101, 9 pages.

Konkel KF, et al., "Results of metallic Hemi-Great Toe Implant for Grade III and early Grade IV hallux rigidus." Foot Ankle Int, 2009;30(7):653-660.

Maffulli N, et al., "Quantitative review of operative management of hallux rigidus." Br Med Bull 2011;98:75-98.

Mann RA, et al., "Hallux rigidus: treatment by cheilectomy." J Bone Joint Surg Am 1988; 70(3):400-406.

Nagy MT, et al., "Second-Generation Ceramic First Metatarsophalangeal Joint Replacement for Hallux Rigidus." Foot Ankle Int. Jul. 1, 2014;35(7):690-698.

Non-Final Office Action dated May 31, 2019 in U.S. Appl. No. 15/542,009, 22 pages.

Papagelopoulos PJ, et al., "Survivorship analysis of implant arthroplasty for the first metatarsophalangeal joint." Clin Orthop Relat Res 1994;(302):164-172.

Raikin SM, et al., "Comparison of arthrodesis and metallic hemiarthroplasty of the hallux metatarsophalangeal joint." J Bone Joint Surg Am 2007;89(9):1979-1985.

Shereff MJ, et al., "Hallux rigidus and osteoarthrosis of the first metatarsophalangeal joint." J Bone Joint Surg Am 1998;80(6):898-908.

Smith K, et al., "Mechanical comparison of cortical screw fixation versus locking plate fixation in first metatarsal base osteotomy." J Foot Ankle Surg. Sep.-Oct. 2014;53(5):529-33.

Sorbie C, et al., "Hemiarthroplasty in the treatment of hallux rigidus." Foot Ankle Int, 2008;29(3):273-281.

Swanson AB, et al., "Use of grommets for flexible hinge implant arthroplasty of the great toe." Clin Orthop Relat Res 1997;(340):87-94.

Townley C.O., et al., "A metallic hemiarthroplasty resurfacing prosthesis for the hallux metatarsophalangeal joint.", Foot Ankle Int, 1994; 15(11):575-580.

Van Saase et al., "Osteoarthritis and obesity in the general population. A relationship calling for an explanation." J Rheumatol,1988;15(7):1152-1158.

* cited by examiner

DEVICES AND METHODS FOR METATARSOPHALANGEAL ARTHROPLASTY PROCEDURES

STATEMENT REGARDING FEDERALLY SPONSORED RESEARCH

This invention was made with government support under Grant No. R21 AR069283, awarded by the National Institutes of Health. The government has certain rights in the invention.

TECHNICAL FIELD

The present technology is generally related to devices and methods for arthroplasty procedures. In particular, several embodiments of the present technology are directed to devices and methods for arthroplasty of the metatarsophalangeal joint.

BACKGROUND

Osteoarthritis ("OA"), particularly OA in the main joint of the great toe (i.e., the first metatarsophalangeal joint ("MTPJ1"), is a significant public health problem. According to one study, by 60 years of age radiographically-confirmed MTPJ1 OA is present in approximately 46% of women and 32% of men. Typical presentations include hallux rigidus or hallux limitus with a painful joint, hallux-sesamoid arthritis, hallux valgus, and inflammatory arthritis. Pathology of this small joint can have a major effect on quality of life because patient mobility is compromised by pain and lack of motion.

DETAILED DESCRIPTION

Figure 1:
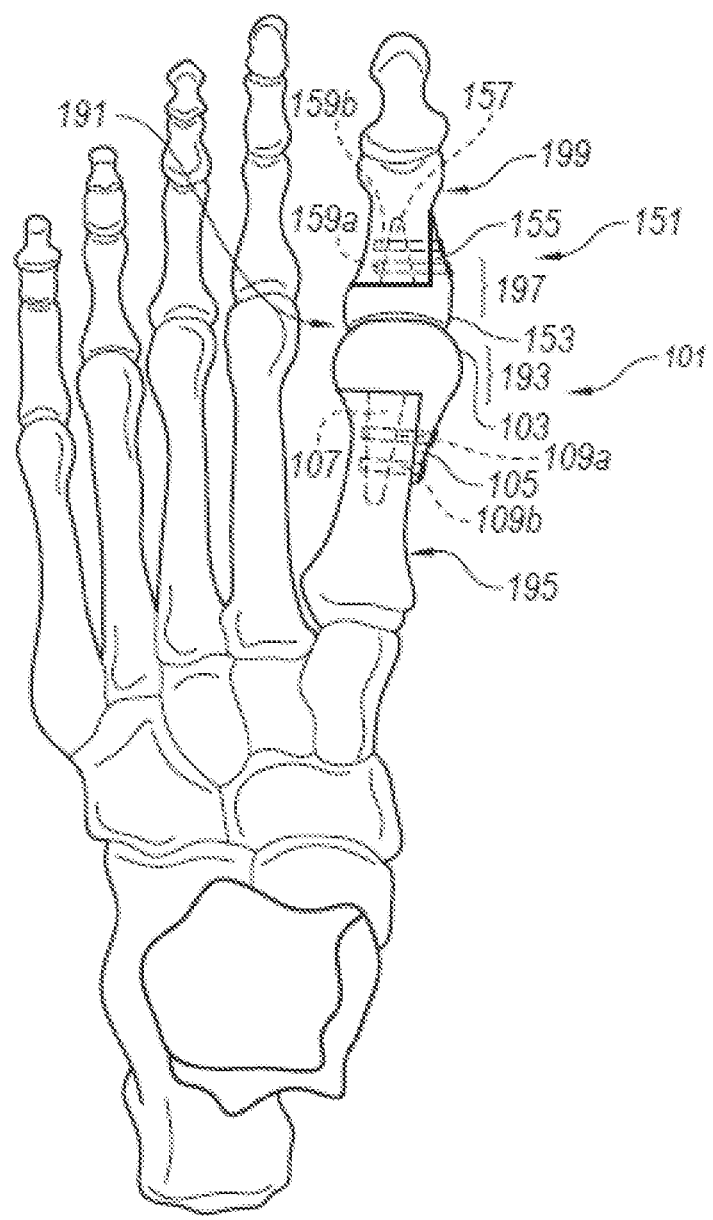
FIG. 1 is a top plan view of first and second arthroplasty devices implanted in a left human foot and configured in accordance with an embodiment of the present technology.

The present disclosure relates generally to devices and methods for arthroplasty of a metatarsophalangeal joint. In particular, the disclosed technology is directed to devices and associated techniques for use during an arthroplasty procedure of the metatarsophalangeal joint. As noted above, osteoarthritis (OA), particularly in the main joint of the great toe (the first metatarsophalangeal joint (MTPJ1)) is a challenging joint to treat. The goals of treatment for OA of the MTPJ1 are to reduce pain and restore mobility of the MTPJ1. When conservative treatment has failed, the two most common surgical options for treatment of OA are removal of damaged articular cartilage and bone (cheilectomy) and, for more severe cases, complete fixation of the joint with trans-articular screws or plates (arthrodesis). Neither of these approaches have high rates of patient satisfaction—particularly among women, who find footwear choices limited after the main toe joint is fixed.

The MTPJ1 is also a challenging joint to replace. The presently available devices to replace all or part of MTPJ1 can be classified into three groups: (1) Single hemi-arthroplasty (e.g., a Futura™ metal hemi toe device); (2) Unconstrained modular arthroplasty for both joint components (e.g., a Medin™ MTP Toe Joint replacement device); or (3) Flexible hinge joints (e.g., a Swanson™ Flexible Hinge Toe). None of these devices, however, have received widespread acceptance from the foot and ankle surgical community; arthrodesis remains the treatment of choice for most surgeons.

Further challenges with replacing the MTPJ1 often arise because there is typically insufficient bone available for fixation using conventional methods, and the loads on the joint are large. At least one study indicates that the median failure/complication rate is 15%, but the upper end of the range is an alarming 93%. In a recent systematic review of outcomes, one author concluded that: "arthrodesis achieves better functional outcomes than total joint replacement" and that "advances still need to be achieved to produce a more successful and anatomical prosthesis that could be functionally superior to an arthrodesis." Brewster, Mark. "Does total joint replacement or arthrodesis of the first metatarsophalangeal joint yield better functional results? A systematic review of the literature." The Journal of Foot and Ankle Surgery 49.6 (2010): 546-552.

An examination of the failure patterns in conventional MTPJ1 joint replacements shows that the most common reported causes of failure are loosening, misalignment, or migration. This is not surprising when the usual techniques of fixation are considered—the components are press- or screw-fitted into the medullary cavity of at least one bone abutting the joint of interest, with or without a polyethylene insert, after reaming of the bone.

Devices configured in accordance with the present technology for use during an arthroplasty procedure of a metatarsophalangeal joint of a patient are expected to address the shortcomings of conventional devices. In one embodiment, for example, a device for use during an arthroplasty procedure of a metatarsophalangeal joint includes an (i) end plate coupled configured and arranged for disposing over a first joint end of a first bone, (ii) a longitudinal plate coupled to the end plate and configured and arranged for disposing along a medial, longitudinal surface of the first bone, and (iii) a stem coupled to the end plate and suitable for extending along an intra-medullary canal of the first bone. At least one fastener couples the longitudinal plate to the stem, the at least one fastener extending at least partially through a longitudinal surface of the first bone.

Further embodiments of the present technology are also directed to methods of performing an arthroplasty procedure on a joint of a human patient. One method can include, for example, removing a portion of a first joint end of a first bone and coupling an implant to the first joint end of the first bone. The implant is coupled such that (a) a stem of the implant is disposed within an intra-medullary canal of the first bone, (b) an end plate of the implant is disposed over the first joint end of the first bone, and (c) a longitudinal plate of the implant is disposed along a medial, longitudinal surface of the first bone. The method can further include extending a fastener between the longitudinal plate and the stem, with the fastener passing through the longitudinal surface of the first bone.

Further specific details of several embodiments of the present technology are described below with reference to FIGS. 1-8. Although many of the embodiments are described below with respect to devices, systems, and methods for arthroplasty procedures, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

As used herein, the terms "distal" and "proximal" refer to the location of the referenced element with respect to the tarsal bones of the patient's foot near the ankle. "Proximal" refers to a location closer to the tarsal bones/ankle, and "distal" refers to a location farther away from the tarsal bones/ankle toward the phalanges (the bones of the toes).

Selected Embodiments of Devices and Methods for Arthroplasty Procedures

FIG. 1 is a top plan view of first and second arthroplasty devices 101 and 151 implanted in a left foot of a human patient and configured in accordance with an embodiment of the present technology. As illustrated, the first arthroplasty device 101 and the second arthroplasty device 151 are implanted at the metatarsophalangeal joint (MTPJ1) 191 of the great toe. In particular, the first arthroplasty device 101 is coupled to a distal end region 193 of a metatarsal bone 195 and the second arthroplasty device 151 is coupled to a proximal end region 197 of a proximal phalanx bone 199 of the patient.

The first arthroplasty device 101 includes an end plate 103 disposed over the distal end region 193 of the metatarsal bone 195. A longitudinal plate 105 extends from the end plate 103 proximally away from the end plate 103 along a medial surface of the metatarsal bone 195. A stem 107 (shown in broken lines) also extends proximally from the end plate 103 along the intramedullary canal of the metatarsal bone 195. Fasteners 109a and 109b (shown in broken lines) can be inserted through holes (FIGS. 2A and 2B) in the longitudinal plate 105 and the stem 107 and obtain purchase in the lateral cortex of the metatarsal bone 195. In some embodiments, the fasteners 109a-b are locking screws. In other embodiments, however, the fasteners 109a-b may have a different configuration.

The second arthroplasty device 151 can be configured similarly to the first arthroplasty device 101. For example, the second arthroplasty device 151 includes an end plate 153 disposed over the proximal end region 197 of the proximal phalanx bone 199. The end plate 153 of the second arthroplasty device 151 is configured to engage with the end plate 103 of the first arthroplasty device 101. A longitudinal plate 155 extends distally away from the end plate 153 along a medial surface of the proximal phalanx bone 199. A stem 157 extends distally from the end plate 153 along the intramedullary canal of the proximal phalanx bone 199. Fasteners 159a and 159b (shown in broken lines) extend through the longitudinal plate 155 and the stem 157 and couple the longitudinal plate 155 to the proximal phalanx bone 199. For example, the fasteners 159a and 159b can be inserted through holes (not shown) in the longitudinal plate 155 and the stem 157 and gain purchase in the lateral cortex of the proximal phalanx bone 199.

The surfaces of the end plates 103 and 153 are complementary to allow for the surfaces to mate with one another while allowing the two to articulate with respect to one another. In some embodiments, for example, the surface of the end plate 103 of the first arthroplasty device 101 is convex and the surface of the end plate 153 of the second arthroplasty device 151 is concave. In other embodiments, however, the shapes of the end surfaces can be reversed (i.e., the surface of end plate 103 may be concave and surface of end plate 153 may be convex). In another embodiment, the surface of the end plate 103 of the first arthroplasty device 101 has a shape corresponding to the natural shape of the metatarsal bone 195 and the surface of the end plate 153 of the second arthroplasty device 151 has a shape corresponding to the natural shape of the proximal phalanx bone 199. In some embodiments, the complementary shapes for the articular surfaces may be patient-specific surfaces based on previously obtained information from a CT scan or other imaging technique. While such personalization may be attractive in some cases, in other embodiments generic articular surface shapes over an anticipated size range are used.

It will be appreciated that although FIG. 1 illustrates a foot with both the first arthroplasty device 101 and the second arthroplasty device 151 installed, in other embodiments only one of the two devices (the first arthroplasty device 101 or the second arthroplasty device 151) may be installed (e.g., hemiarthroplasty). Further, while the arrangement in FIG. 1 shows the longitudinal plates 105 and 155 of the first and second arthroplasty devices 101 and 151, respectively, installed on a medial side of the corresponding bones, in other embodiments the devices could be attached to other surfaces of the bone.

FIGS. 2A-2D are enlarged isometric, top, proximal, and medial views, respectively, of the first arthroplasty device 101 of FIG. 1 adjacent to a prepared metatarsal bone 195. For purposes of clarity, the metatarsal bone 195 is omitted from the proximal view in FIG. 2C, and fasteners 109a-b are omitted from FIGS. 2C and 2D. Referring to FIGS. 2A-2D together, the first arthroplasty device 101 includes end plate 103 and longitudinal plate 105 extending proximally away from the end plate 103. The stem 107 extends proximally away from the end plate 103, approximately parallel to the longitudinal plate 105. In the illustrated embodiment, the end plate 103, longitudinal plate 105, and stem 107 are integrally formed. In other embodiments, however, the components of the first arthroplasty device 101 may be individual components that are coupled together before installation.

The longitudinal plate 105 includes one or more holes or apertures 110 (two are shown) for receiving fastener(s), such as fasteners 109a-b, to secure the first arthroplasty device 101 in place relative to the bone 195. The stem 107 can also include one or more corresponding holes or apertures 111 aligned with the holes 110 to receive the fastener(s) and allow the fastener(s) to pass through to obtain purchase in the opposite bone cortex. In some embodiments, the holes 111 in the stem 107 may be oversized relative to the holes 110 and fasteners 109a-b. Although the holes 110 are shown with a raised profile in the illustrated embodiment, in other embodiments the holes 110 may be countersunk relative to the surface of the longitudinal plate 105 such that when the fasteners 109a-b are installed therethrough, the fastener heads are flush with the surface of the longitudinal plate 105.

Figure 2A:
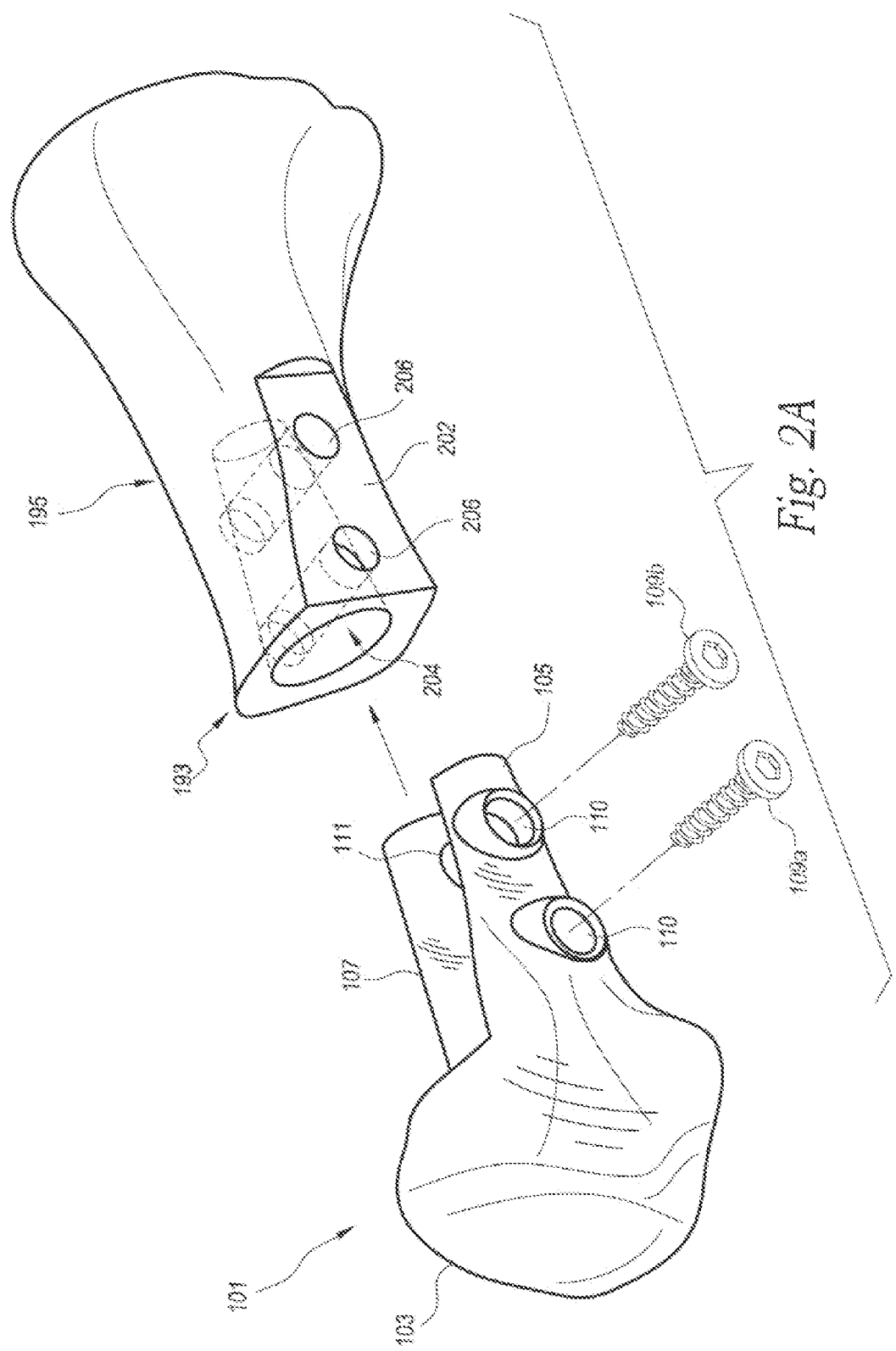
FIGS. 2A-2D illustrate various views of the first arthroplasty device of FIG. 1 configured in accordance with an embodiment of the present technology.
Figure 2B:
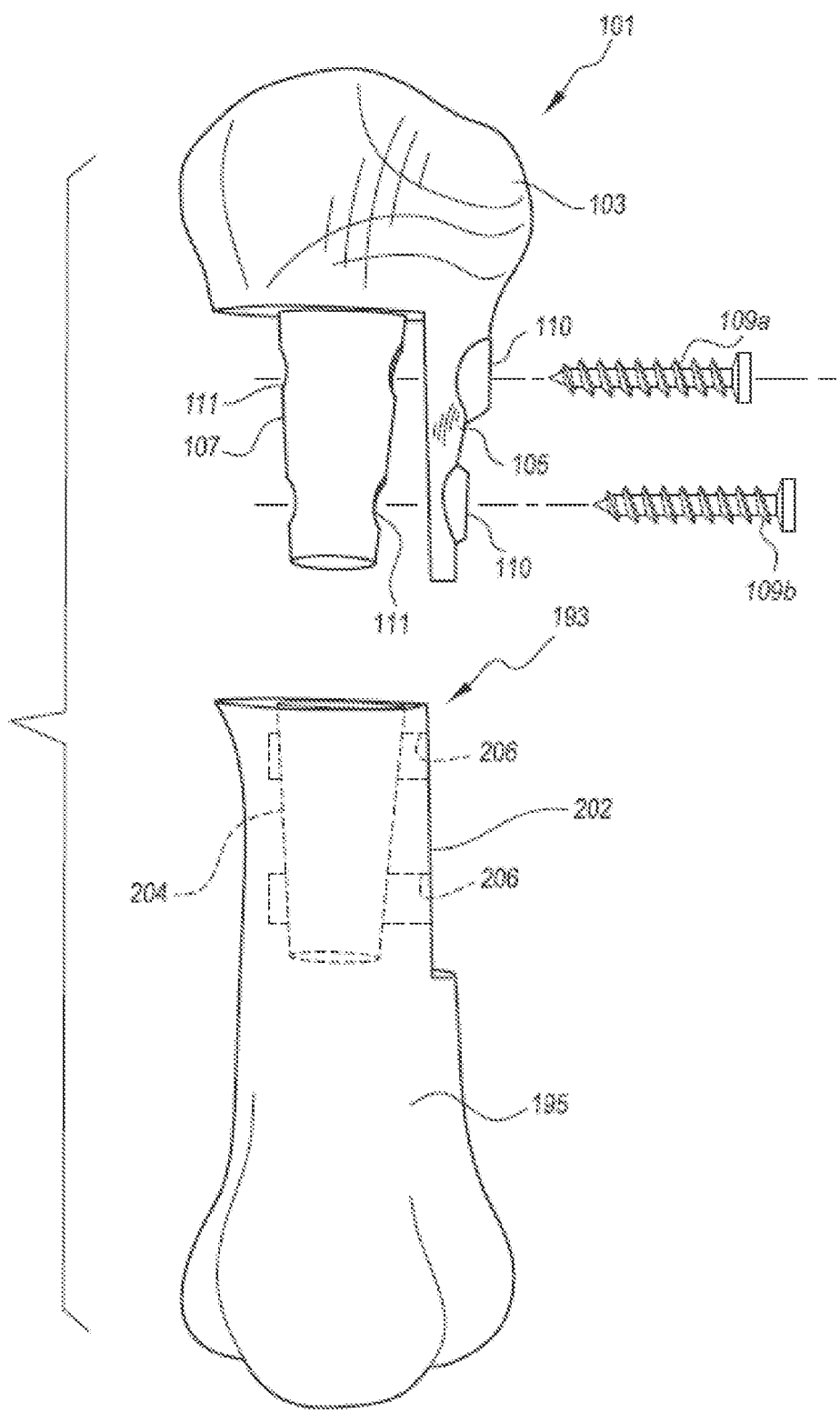
Figure 2C:
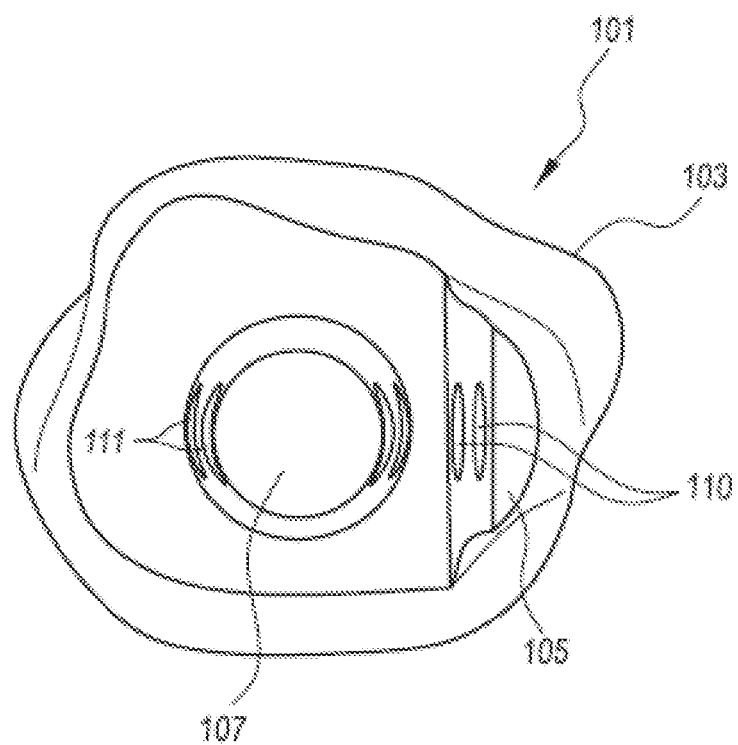
Figure 2D:
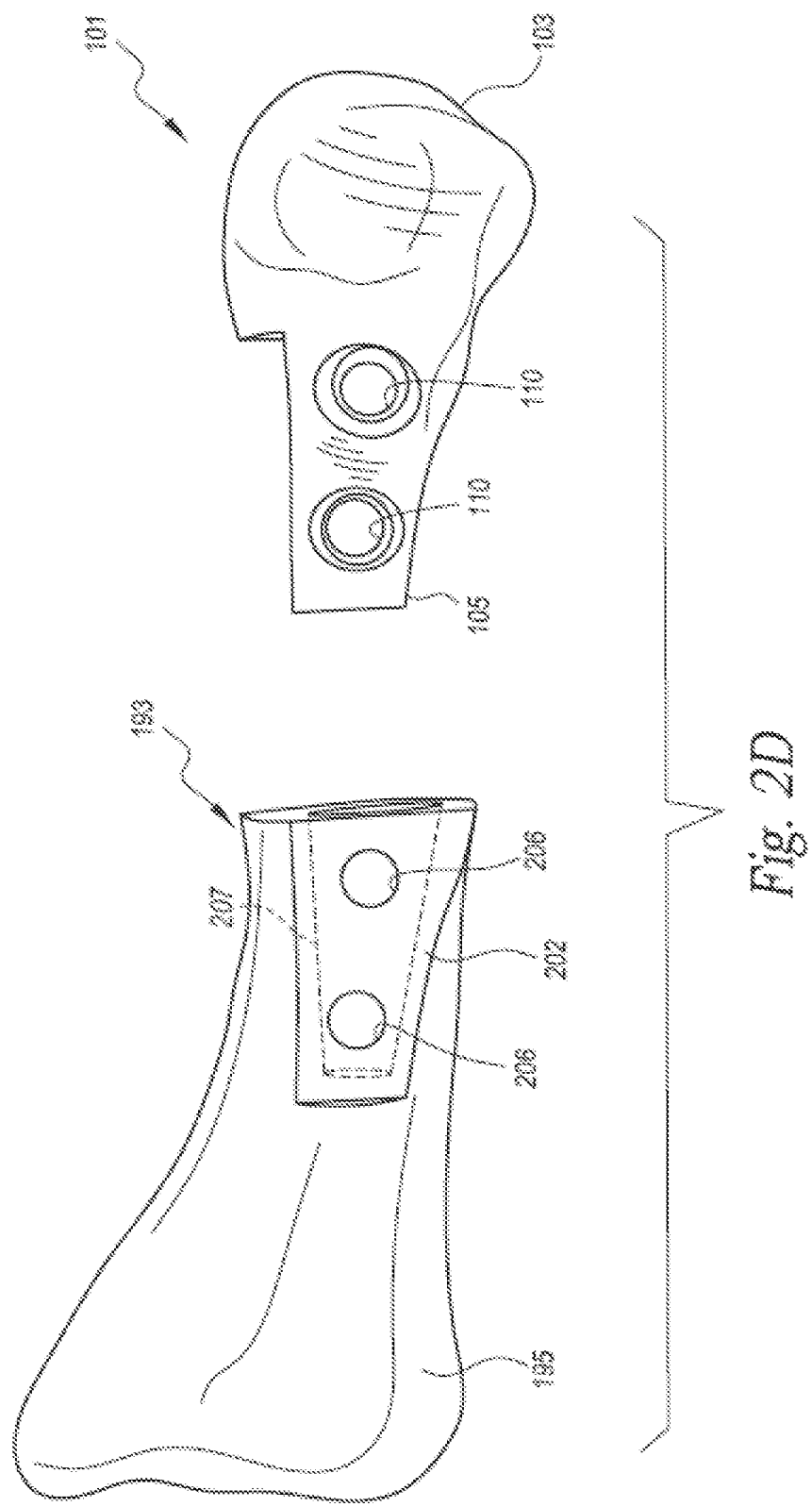

As best seen in FIGS. 2A and 2B, in order to prepare the metatarsal bone 195 to receive the first arthroplasty device 101, a surgical template or guide (not shown) may be used. For example, the surgical template can be used by the surgeon when removing/shaping the distal end region 193 of the bone 195 that will be replaced by the end plate 103 of the first arthroplasty device 101. The surgical template can also be used to shape a medial portion 202 of the bone 195 to accommodate the longitudinal plate 105 of the first arthroplasty device 101. Further, a reamer may be used to create a void 204 (e.g., a conical void) shaped and sized for receiving the stem 107 therein when the first arthroplasty device 101 is mated with the metatarsal bone 195.

Guide hole(s) 206 for fastener insertion may also be formed in the metatarsal bone 195 substantially perpendicular to the long axis of the bone 195, and configured to intersect with the void 204. In the illustrated embodiment, two guide holes 206 have been formed and shaped/sized to correspond to holes 110 when the first arthroplasty device 101 is installed.

During installation, the first arthroplasty device 101 is mated with the prepared metatarsal bone 195. In at least some embodiments, the first arthroplasty device 101 may tapped into place. When the first arthroplasty device 101 in in place relative to the bone 195, the fasteners 109a and 109b are inserted through the holes 110 in the longitudinal plate 105 and through the guide holes 206 in the metatarsal bone 195. As best seen in FIGS. 2A and 2B, the fasteners 109a-b are sized and shaped to extend through the holes 110 and the oversized holes 111 in the stem to couple the longitudinal plate 105 to the metatarsal bone 195. When installed (and as noted above with reference to FIG. 1), the fasteners 109a-b also extend partially through the metatarsal bone 195 and gain purchase in the lateral cortex of the metatarsal bone 195.

One feature of the first arthroplasty device 101 is that, when installed, the stem 107 and longitudinal plate 105 are coupled together via at least one fastener 109. This feature is expected to reduce or inhibit the problems experienced by many conventional devices associated with loosening, misalignment, and/or migration of the implant. Further, because the fasteners 109a-b gain purchase though a relatively significant portion of the bone 195, the first arthroplasty device 101 is expected to be able to handle the large loads on the MTPJ1 joint with less complications/failures than conventional devices.

Figure 3B:
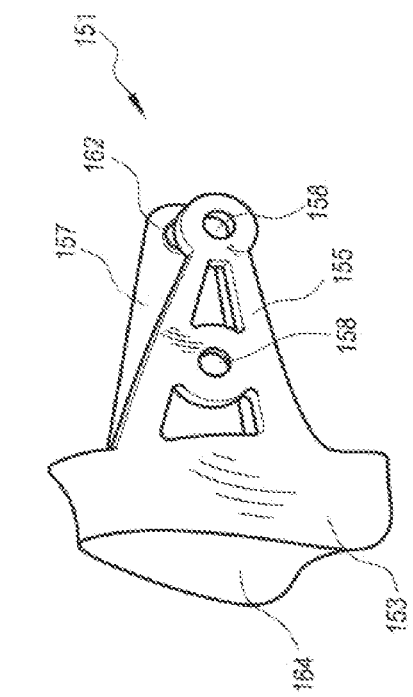
FIGS. 3A-3D illustrate various views of the second arthroplasty device of FIG. 1 configured in accordance with an embodiment of the present technology.
Figure 3D:
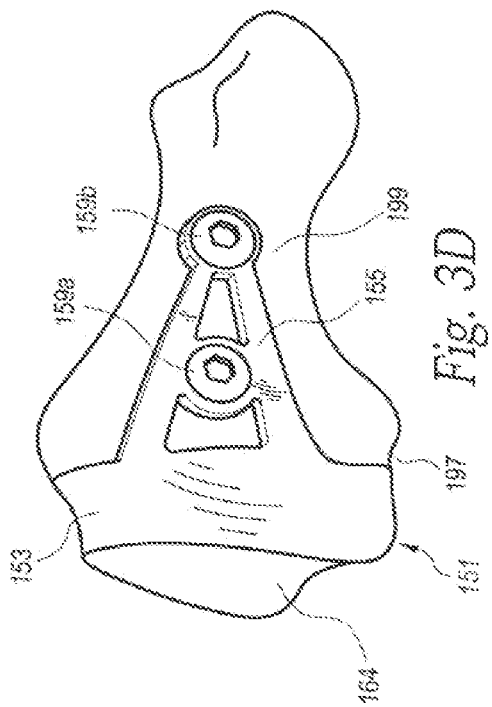
Figure 3A:
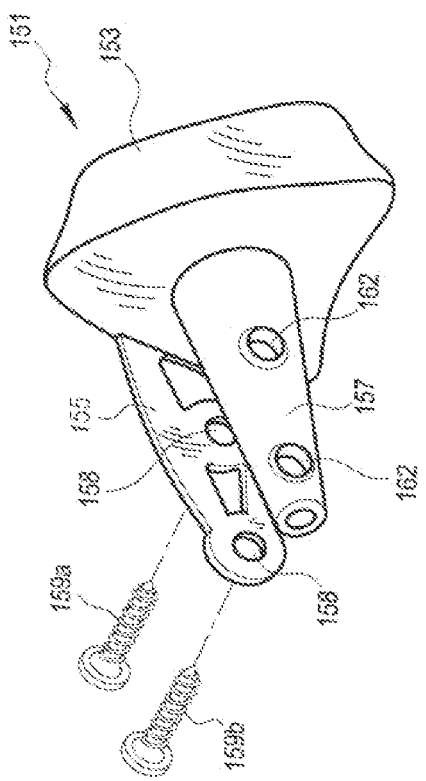

FIGS. 3A-3D illustrate various views of the second arthroplasty device 151 configured in accordance with an embodiment of the present technology. In particular, FIGS. 3A and 3B are enlarged, isometric views of the second arthroplasty device 151 before installation. For purposes of clarity, the proximal phalanx bone 199 is omitted from FIGS. 3A and 3B. Referring to FIGS. 3A and 3B together, the second arthroplasty device 151 includes a number features similar to the features of the first arthroplasty device 101 described above with reference to FIGS. 1-2D. For example, as noted previously, the second arthroplasty device 151 includes end plate 153 and longitudinal plate 155 extending distally away from the end plate 153. The end plate 153 of the second arthroplasty device 151 has a concave arrangement configured to engage with the convex surface of the end plate 103 of the first arthroplasty device 101 (FIG. 1). The second arthroplasty device 151 also includes stem 157 extending away from the end plate 153, approximately parallel to the longitudinal plate 155. In the illustrated embodiment, the end plate 153, longitudinal plate 155, and stem 157 of the second arthroplasty device 151 are integrally formed. In other embodiments, however, the components of the second arthroplasty device 151 may be individual components that are coupled together before installation. Further, in the illustrated embodiment there are voids in the longitudinal plate 155, but in other embodiments there may be no voids in the longitudinal plate 155.

The longitudinal plate 155 includes one or more holes or apertures 158 (two are shown) for receiving fastener(s), such as fasteners 159a-b, to secure the second arthroplasty device 151 in place relative to the bone 199 (FIG. 3D). The stem 157 can also include one or more corresponding holes or apertures 162 aligned with the holes 158 to receive a portion of the fastener(s) 159.

Figure 3C:
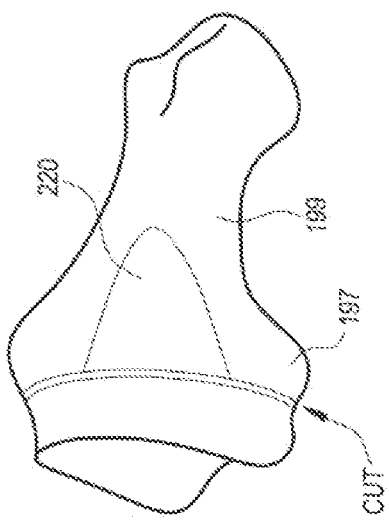
Figure 4A:
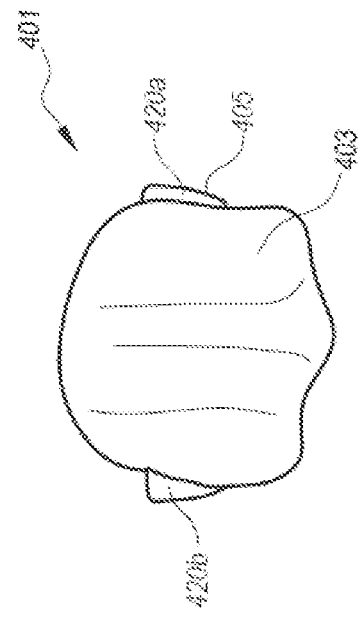
FIGS. 4A-4D illustrate various views of a first arthroplasty device configured in accordance with another embodiment of the present technology.
Figure 4B:
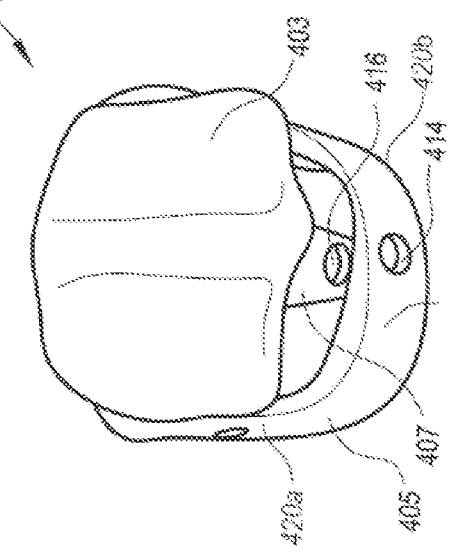
Figure 4C:
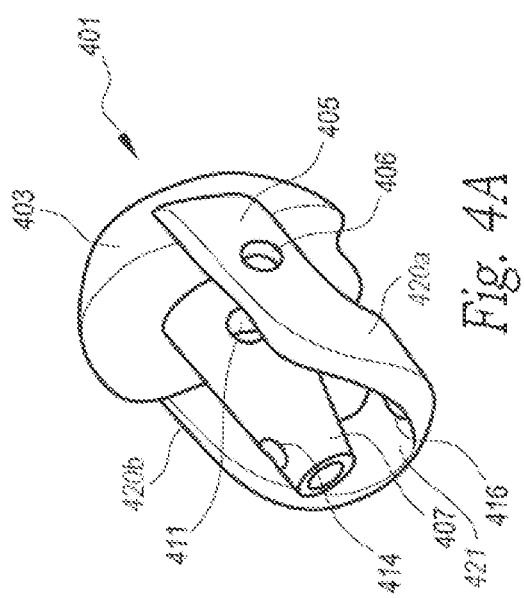
Figure 4D:
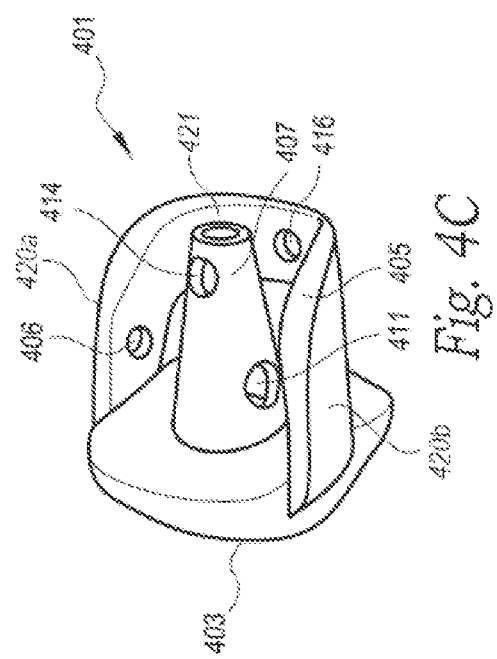

FIG. 3C is an exploded isometric view of the proximal phalanx bone 199 prior to receiving the second arthroplasty device 151, and FIG. 3D illustrates the second arthroplasty device 151 installed with the proximal phalanx bone 199. Referring first to FIG. 3C, a surgical template or guide (not shown) may be used to prepare the proximal phalanx bone 199 for installation. The process can be similar to that described above with reference to the metatarsal bone 195. For example, the surgical template can be used for cutting/shaping the proximal end region 197 of the bone 199 to receive the second arthroplasty device 151. A medial portion 220 of the bone 199 may also shaved/shaped to receive the longitudinal plate 155. Further, a void (not seen in FIG. 3C) can be created in the bone 199 to receive the stem 157 therein during installation. Guide holes (not seen in FIGS. 3C and 3D) are also formed and shaped/sized to correspond to holes 158/162 when the second arthroplasty device 151 is installed.

As best seen in FIG. 3D, once the second arthroplasty device 151 is mated with and positioned as desired relative to the proximal end region 197 of the bone 199, fasteners 159a-b can be installed through the holes 158 in the longitudinal plate 155 and the corresponding holes 162 in the stem 157 (FIGS. 3A and 3B). Although the fasteners 159a-b are shown with slightly raised profile after installation in FIG. 3D, in other embodiments the holes 158 (FIG. 3B) may be countersunk relative to the surface of the longitudinal plate 155 such that when the fasteners 159a-b are installed therethrough, the fastener heads are flush with the surface of the longitudinal plate 155.

As with the first arthroplasty device 101 described above, the fasteners 159a and 159b gain purchase in the lateral cortex of the proximal phalanx bone 199 and help reduce/inhibit loosening, misalignment, and/or migration of the device after implantation.

Selected Embodiments of Dual-Component Devices and Methods for Arthroplasty Procedures The arthroplasty devices described above with respect to FIGS. 1-4D can each be single component devices in which a unitary implant is positioned against the bone and fixed in place via one or more fasteners. Although there are benefits of a single-component device (such as simplicity of operation and manufacture), there are also certain limitations associated with such single-component devices. For example, because both the stem and the longitudinal plate must be positioned at the same time and in parallel, the longitudinal plate cannot taper inwardly along its length towards the stem. Rather, with single-component devices, the longitudinal plate and the stem must be parallel or diverge as they extend away from the end plate in order to facilitate the sliding motion of inserting the device into place. Additionally, single-component devices must be appropriately sized along each of the stem, the end plate, and the longitudinal plate together.

Figure 5:
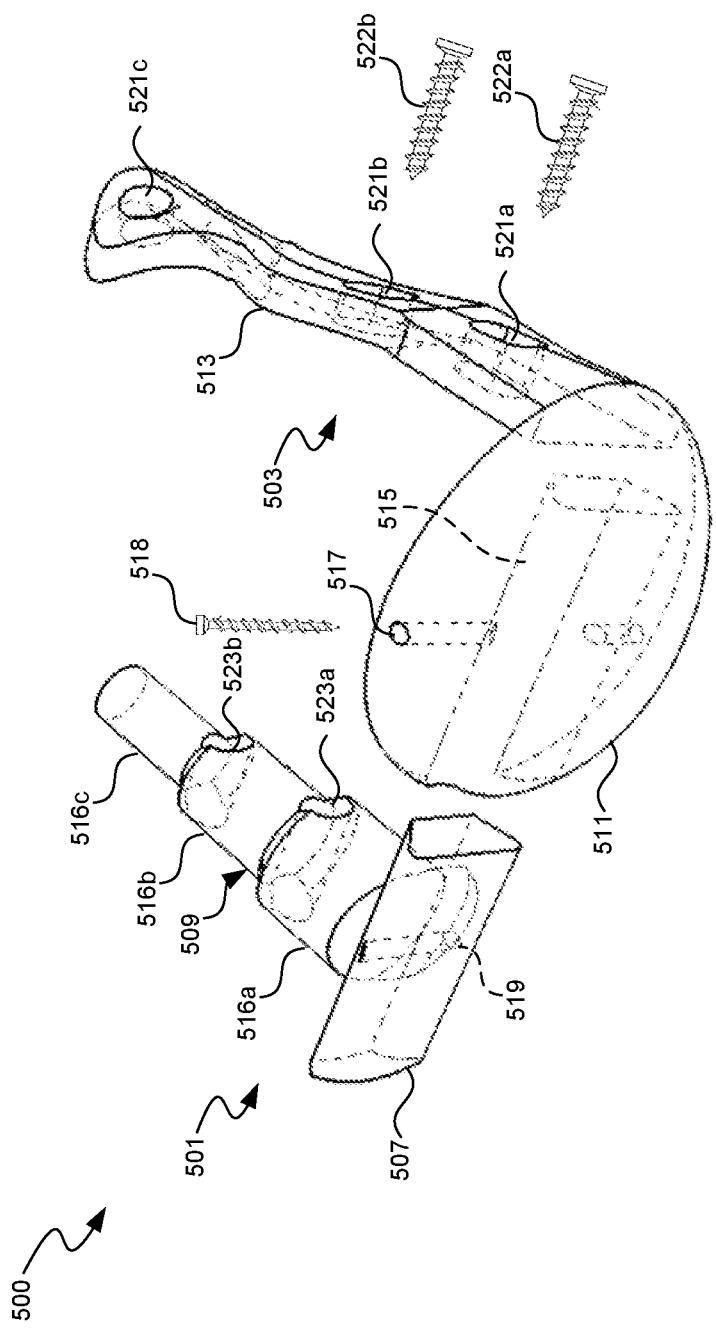
FIG. 5 illustrates a dual-component arthroplasty device configured in accordance with another embodiment of the present technology.
Figure 6:
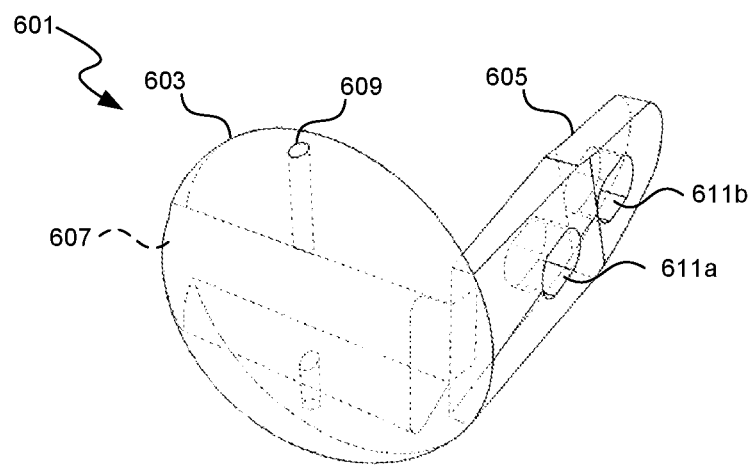
FIG. 6 illustrates one component of a dual-component arthroplasty device configured in accordance with another embodiment of the present technology.
Figure 7:
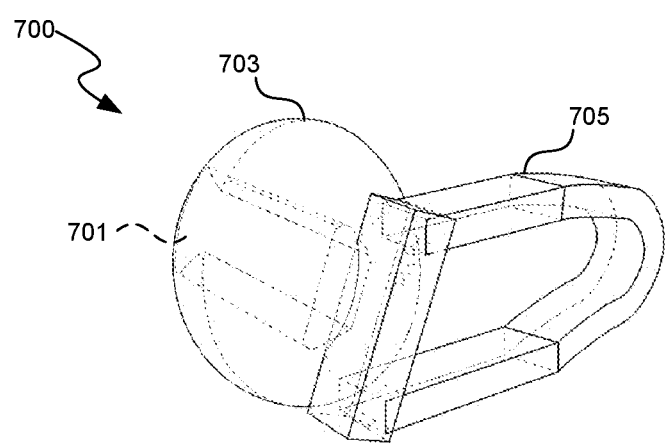
FIG. 7 illustrates a cutting guide for use with the arthroplasty device of FIG. 6.

Embodiments of arthroplasty devices described below with respect to FIGS. 5-7 are directed to dual-component devices that provide certain advantages in selected patients over single-component arthroplasty devices. For example, and as described in more detail below, dual-component devices are expected to enable placement of longitudinal plates that taper inwardly toward the stem along their length without the mechanical interference faced by single-component devices. Additionally, dual-component devices can decouple the sizing of the stem component from the end plate and longitudinal plate component, such that a single stem component can be mated with a number of differently sized end plate and longitudinal plate components. This variability is expected to provide more options for sizing to accommodate the anatomy of a particular patient, thereby improving fit and patient outcomes.

FIG. 5 illustrates a dual-component arthroplasty device configured in accordance with an embodiment of the present technology. As illustrated, the device 500 includes a first component 501 and a second component 503. The first and second components 501 and 503 can be removably mated or engaged together as described in more detail below. In use, the first component 501 can first be inserted into the intramedullary canal of a bone (not shown), then the second component 503 can be slidably coupled or otherwise mated with the first component. Although the illustrated embodiment includes a convex outer surface (for example, configured to be placed over a distal end region of a metatarsal bone of the MTPJ1), in other embodiments the outer surface can be concave (for example, configured to be placed over the proximal end region of a proximal phalanx bone of the MTPJ1). In some embodiments, the outer surface has a shape corresponding to the natural shape of the metatarsal bone or to the natural shape of the proximal phalanx bone. In other embodiments, the complementary shapes for the articular surfaces may be patient-specific surfaces based on previously obtained information from a CT scan or other imaging technique. While such personalization may be attractive in some cases, in other embodiments generic articular surface shapes over an anticipated size range are used. As with the embodiments described above with respect to FIGS. 1-2D, the bone receiving the device 500 thereon can be prepared by cutting away a predetermined portion of the bone before insertion of the device 500.

The first component 501 includes an attachment fitting 507 and a stem 509 extending away from the attachment fitting 507. The second component 503 includes an end plate 511 and a longitudinal plate 513 extending away from the end plate 511. In the coupled configuration, the attachment fitting 507 is slidably mated with a recess 515 within the end plate 511. In the illustrated embodiment, the attachment fitting 507 has a generally trapezoidal prism shape, and the recess 515 has a corresponding shape sized and configured to receive the attachment fitting 507 therein. This configuration can provide a mortise and tenon joint in which the attachment fitting is the mortise and the end plate with the recess is the tenon. In some embodiments, the mortise and tenon joint can taper. In other embodiments, the shape and dimensions of the attachment fitting 507 and the recess 515 can take a variety of forms, for example the attachment fitting 507 can be a protrusion having a rectangular, elliptical, circular, irregular polygonal, or any other cross-sectional shape, and the recess 515 can assume a corresponding shape configured to slidably receive the attachment fitting 507 therein. Although the illustrated embodiment facilitates sliding engagement of the attachment fitting 507 and the recess 515, in other embodiments the mating can be a snap-fit, rotatable coupling, or any other configuration that permits removable mating of the attachment fitting 507 and the recess 515.

The stem 509 can have a tapered profile such that a proximal portion closest to the attachment fitting 507 has a larger cross-sectional dimension than a distal portion furthest from the attachment fitting 507. This tapered profile can facilitate insertion of the stem 509 within a prepared intramedullary canal of a target bone. In the illustrated embodiment, for example, the stem 509 has a tiered profile that includes three sections 516a-c having distinct cross-sectional sizes. The first section 516a is directly adjacent to the attachment fitting 507 and has the largest cross-sectional dimension. The second section 516b adjacent to the first section 516a has a smaller cross-sectional dimension than the first section 516a, and the third and distalmost section 516c has a yet smaller cross-sectional dimension, so that the overall profile of the stem 509 tapers inwardly as it extends way from the attachment fitting 507. In the illustrated embodiment, each section 516a-c has a substantially uniform cross-sectional dimension. However, in other embodiments, each section can itself taper or have any other non-uniform cross-sectional dimension, with defined steps disposed between adjacent sections. In some embodiments, the number of sections of the tiered stem 509 can vary, for example two, three, four, five, or more discrete sections. This tiered profile can provide improved purchase of the stem 509 with respect to the intramedullary canal of the target bone, and can facilitate tapping the stem 509 into position.

As described in more detail below with respect to FIG. 7, in some embodiments the first component 501 can be used as a fixed point to mount surgical guides prior to coupling the second component 503 in position. For example, once the first component 501 is inserted (e.g., the stem 509 is inserted into a prepared intramedullary canal of a target bone and the attachment fitting 507 protrudes from an end of the target bone), a surgical guide can be coupled to the attachment fitting 507 in a manner similar to the coupling of the second component 503. For example, a surgical guide can have a recess configured to removably mate with the attachment fitting 507. This mating provides a secure positioning and reliably reference point for placement of the surgical guide, which can then be used to remove additional bone regions in order to fi the implant before the second component 503 is installed.

The end plate 511 of the second component 503 can include a hole or aperture 517 therein that intersects with the recess 515, and the attachment fitting 507 can include a corresponding hole or aperture 519 configured to align with the hole 517 of the end plate 511 when the attachment fitting 507 is received within the recess 515. In use, the first component 501 can be coupled to the second component 503 by sliding the end plate 511 over the attachment fitting 507 such that the attachment fitting 507 is fully received within the recess 515. Once in position, a fastener 518 can be inserted through both the hole 517 in the end plate 511 and through the hole 519 in the attachment fitting 507. This fastener serves to lock the attachment fitting 507 and the end plate 511 together, thereby preventing sliding movement and decoupling of the first component 501 and the second component 503 after implantation. In some embodiments, an additional fixation mechanism can be employed. The additional fixation mechanism can include, for example, an adhesive disposed in or around the recess 515 and/or the attachment fitting 507 or another suitable fixation mechanism.

The longitudinal plate 513 can have a contoured shape configured to be flush with an outer surface of the target bone after implantation of the device 500. In the illustrated embodiment, the longitudinal plate 513 has a length that extends beyond the length of the stem 509. Additionally, the longitudinal plate 513 tapers inwardly towards the stem 509 when the first component 501 and the second component 503 are coupled together. This tapering can provide a better correspondence between the longitudinal plate 513 and the outer surface (e.g., the medial aspect) of the target bone, which can enable the increased length of the longitudinal plate 513 as compared to embodiments in which the longitudinal plate is parallel to the stem.

Similar to the embodiments described above with respect to FIGS. 1-2D, the longitudinal plate 513 includes a plurality of holes or apertures 521a-c (collectively "holes 517") for receiving fasteners 522a-b therethrough. Inserting fasteners (e.g., screws, nails, or other suitable fasteners) through the holes 517 secures the device 500 to the target bone. The stem 509 can also include one or more corresponding holes or apertures 523a-b (collectively "holes 523") aligned with the holes 517 to receive the fasteners and allow the fasteners to pass through to obtain purchase in the opposite bone cortex. In the illustrated embodiment, the stem 509 includes two holes 523a-b that are configured to be aligned with two holes 521a-b, respectively, through the longitudinal plate 513. The third hole 521c is at a position on the longitudinal plate 513 that is beyond the end of the stem 509. A fastener inserted through this third hole 521c can be inserted into the bone to provide additional purchase without intersecting a corresponding hole through the stem 509. In some embodiments, the holes 523 in the stem 509 may be oversized relative to the holes 521 and the fasteners. In some embodiments, the holes 521 may be countersunk relative to the surface of the longitudinal plate 513 such that when the fasteners are installed therethrough, the fastener heads are flush with the surface of the longitudinal plate 513.

FIG. 6 illustrates one component 601 of a dual-component arthroplasty device configured in accordance with another embodiment of the present technology, and FIG. 7 illustrates a cutting guide 700 for use with the arthroplasty device of FIG. 6. The component 601 can be generally similar to the second component 503 described above with respect to FIG. 5, except that the component has a shorter longitudinal plate 605.

The component 601 includes an end plate 603 and a longitudinal plate 605 extending away from the end plate 603. The end plate 603 includes a recess 607 formed therein. The recess 607 can be sized and configured to removably receive a corresponding attachment fitting therein. In the illustrated embodiment, the recess 607 is sized to receive an attachment fitting having a generally trapezoidal prism shape, though the shape and dimensions of the recess 607 can vary in other embodiments. The end plate 603 can include a hole or aperture 609 therein that intersects with the recess 607. As described above with respect to FIG. 5, the hole 609 can be aligned with a corresponding hole in an attachment fitting when received within the recess 607, and a fastener (not shown) can be inserted through both holes to lock the attachment fitting within the recess 607.

The longitudinal plate 605 includes a plurality of holes or apertures 611a-b (collectively "holes 611") for receiving fasteners (not shown) therethrough. Inserting fasteners through the holes 611 secures the component 601 to the bone. Additionally, when used with a corresponding component having a stem with aligned holes therein, the fasteners can be inserted through the holes 611 in the longitudinal plate 605 and through holes in the stem to secure the components together. In the illustrated embodiment, the longitudinal plate 605 is shorter than that of FIG. 5, including only two holes 611. Depending on patient anatomy and the target bone, a shorter longitudinal plate 605 may be preferred.

As described above with respect to FIG. 5, in operation a component having a stem and attachment fitting can first be inserted into a prepared intramedullary canal of the target bone. Prior to coupling the component 601 to the attachment fitting, the cutting guide 700 shown in FIG. 7 can be used. For example, the cutting guide 700 can be slidably coupled to the attachment fitting via the recess 701, similar to the operation of the first and second components 501 and 503 described above. The recess 701 can be disposed within an end plate 703, and a guide member 705 can extend away from the end plate 703. Once the cutting guide 700 is coupled to the attachment fitting, the operator can use a drill or other cutting device to remove bone using the guide member 705. In particular, the exposed area of bone circumscribed by the guide member 705 can be removed to a desired depth, leaving an indentation in the target bone. This indentation can correspond to the shape of the longitudinal plate 605 such that, when the cutting guide 700 is removed and the component 601 is coupled to the attachment fitting, the longitudinal plate 605 of the component 601 is substantially received within the indentation in the target bone. As a result, the longitudinal plate 605 can rest flush with the outer surface of the target bone. In other embodiments, the longitudinal plate 605 may still protrude from the side surface of the target bone, but the extent of protrusion may be reduced by the use of the cutting guide 700.

Figure 8:
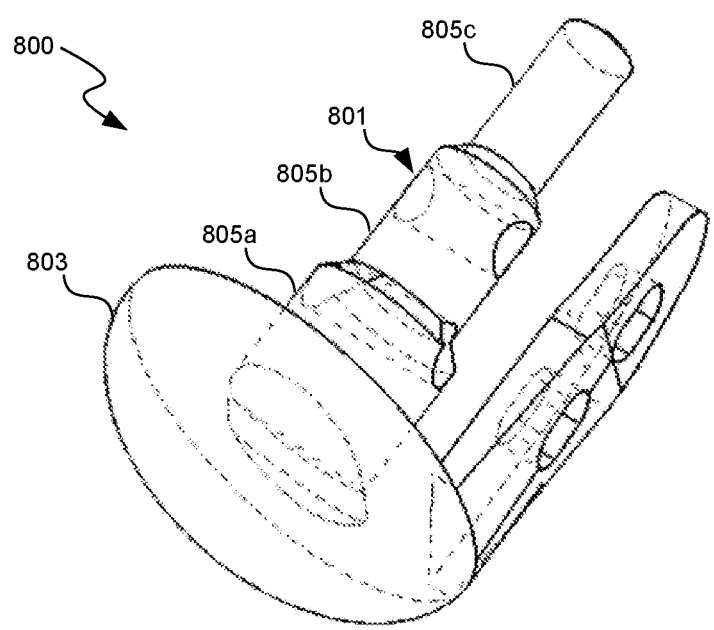
FIG. 8 illustrates another arthroplasty device configured in accordance with another embodiment of the present technology.

FIG. 8 illustrates another arthroplasty device 800 configured in accordance with another embodiment of the present technology. The device 800 can be substantially similar to the first arthroplasty device 101 of FIGS. 1-2D, except that the device 800 includes a stem 801 having a tapered and tiered profile. The stem 801 can taper similar to the stem 509 described above with respect to FIG. 5. For example, the stem 801 can have a tiered profile that includes three sections 805a-c having distinct cross-sectional sizes. The first section 805a is directly adjacent to end plate 803 and has a largest cross-sectional dimension. The second section 805b adjacent to the first section 805a has a smaller cross-sectional dimension than the first section 805a, and the third and distalmost section 805c has a yet smaller cross-sectional dimension, so that the overall profile of the stem 801 tapers inwardly as it extends way from end plate 803. In the illustrated embodiment, each section 805a-c has a substantially uniform cross-sectional dimension. However, in other embodiments, each section can itself taper or have any other non-uniform cross-sectional dimension, with defined steps disposed between adjacent sections. In some embodiments, the number of sections of the tiered stem 801 can vary, for example two, three, four, five, or more discrete sections. This tiered profile can provide improved purchase of the stem 801 with respect to the intramedullary canal of the target bone.

The arthroplasty devices 101/151/401/500/600/800, including the fasteners 109/159 and other referenced fasteners described herein, can be made of a variety of materials including, for example, biocompatible materials such as stainless steel, titanium, and other biocompatible and rigid materials suitable for use in surgical implants.

Further, although the description above refers to the MTPJ1 joint for illustrative purposes, embodiments of the first and second arthroplasty devices and described herein can be suitable for use along any suitable patient joint, for example other metatarsophalangeal joints of the foot, metacarpophalangeal joints of the hand, and any other suitable joint. Moreover, it will be appreciated that the disclosed arthroplasty devices can be modified in many different ways to better accommodate different joints and different anatomies within individual patients. Additionally, although the longitudinal plate is shown on the medial side in the embodiments describe above with reference to FIGS. 1-3D, 5, 6, and 8, in other embodiments the longitudinal plate may attached to other surfaces of the bone in lieu of (or in addition to) the medial surface.

ADDITIONAL EXAMPLES

1. A device for use during an arthroplasty procedure of a joint of a patient, the joint extending between a first joint end of a first bone and an abutting second joint end of a second bone of the patient, the device comprising:
   an end plate configured and arranged for disposing over the first joint end of the first bone;
   a longitudinal plate extending from the end plate and configured and arranged for disposing along a medial, longitudinal surface of the first bone;
   a stem extending from the end plate and suitable for extending along an intra-medullary canal of the first bone; and
   at least one fastener for coupling the longitudinal plate to the first bone, wherein, when the device is installed, the at least one fastener extends at least partially through the longitudinal surface of the first bone.

2. The device of example 1 wherein:
   the joint is a metatarsophalangeal joint;
   the first bone is a metatarsus bone;
   the second bone is an abutting proximal phalanx bone; and the end plate is convex.

3. The device of example 1 wherein:
   the joint is a metatarsophalangeal joint;
   the first bone is a proximal phalanx bone of a foot;
   the second bone is an abutting metatarsal bone; and the end plate is concave.

4. The device of any one of examples 1-3, further comprising a first hole in the longitudinal plate and a second hole in the stem, wherein, when the device is installed, the fastener extends through the first and second holes.

5. The device of example 4, further comprising:
   a third hole in the longitudinal plate and a fourth hole in the stem; and
   a second fastener coupling the longitudinal plate to the stem, wherein the second fastener is configured to extend through the third and fourth holes.

6. The device of any one of examples 1-5 wherein the fastener is a locking screw.

7. The device of any one of examples 1-6, further comprising a second longitudinal plate coupled to the end plate and configured and arranged for disposing along the medial, longitudinal surface of the first bone circumferentially opposite to the first longitudinal plate along the medial, longitudinal surface of the first bone, and wherein, when the device is installed, the fastener couples the first and second longitudinal plates to the first bone.

8. The device of any one of examples 1-7 wherein end plate, the longitudinal plate, and the stem comprise at least one of titanium or stainless steel.

9. The device of any one of examples 1-8 wherein the end plate, the longitudinal plate, and the stem are integrally formed.

10. The device of any one of examples 1-9 wherein the stem is tapered.

11. A device for use during an arthroplasty procedure of a joint of a patient, the joint extending between a first joint end of a first bone and an abutting second joint end of a second bone of the patient, the device comprising:
   an end plate configured to be disposed over the first joint end of the first bone;
   a longitudinal plate extending from the end plate and configured to be disposed along a medial, longitudinal surface of the metatarsus bone, the longitudinal plate having a hole formed therein; and
   a stem extending from the end plate and suitable for extending along an intra-medullary canal of the first bone, the stem having a second hole formed therein, and wherein the first hole and the second hole are aligned.

12. The device of example 11, further comprising a fastener for coupling the longitudinal plate to the first bone, and wherein, when the device is installed, the fastener extends through the first hole and the second hole, passing at least partially through the longitudinal surface of the first bone.

13. The device of example 11 wherein:
   the joint is a metatarsophalangeal joint;
   the first bone is a metatarsus bone;
   the second bone is an abutting proximal phalanx bone; and the end plate is convex.

14. The device of example 11 wherein:
   the joint is a metatarsophalangeal joint;
   the first bone is a proximal phalanx bone of a foot;
   the second bone is an abutting metatarsal bone; and
   the end plate is concave.

15. A method of performing an arthroplasty procedure on a joint of a human patient, the joint extending between a first joint end of a first bone and an abutting second joint end of a second bone of the patient, the method comprising:
   removing a portion of the first joint end of the first bone;
   coupling an implant to the first joint end of the first bone, such that—
      a stem of the implant is disposed within an intra-medullary canal of the first bone;
      an end plate of the implant is disposed over the first joint end of the first bone; and
      a longitudinal plate of the implant is disposed along a medial, longitudinal surface of the first bone; and
   extending a fastener between the longitudinal plate and the stem, the fastener passing through the longitudinal surface of the first bone.

16. The method of example 15, further comprising reaming the intra-medullary canal of the first bone prior to coupling the implant to the first joint end of the first bone.

17. The method of example 15 or example 16 wherein removing the portion of the first joint end of the first bone comprises cutting the portion of the first joint end of the first bone using a surgical template.

18. The method of example 15 wherein the joint is a metatarsophalangeal joint, the first bone is a metatarsus bone, and the second bone is an abutting proximal phalanx bone.

19. The method of example 15 wherein the joint is a metatarsophalangeal joint, the first bone is a proximal phalanx bone of a foot, and the second bone is an abutting metatarsal bone.

20. The method of any one of examples 15-19, further comprising:
drilling a hole through at least a portion of the first bone prior to extending the fastener; and
passing the fastener through the hole.

21. A device for use during an arthroplasty procedure of a joint of a patient, the joint extending between a first joint end of a first bone and an abutting second joint end of a second bone of the patient, the device comprising:
a first component comprising:
an attachment fitting configured for disposing over the first joint end of the first bone; and
a stem extending from the attachment fitting and suitable for extending along an intra-medullary canal of the first bone;
a second component comprising:
an end plate configured to mate with the attachment fitting; and
a longitudinal plate extending from the end plate and configured for disposing along a medial, longitudinal surface of the first bone; and
at least one fastener for coupling the longitudinal plate to the first bone.

22. The device of example 21 wherein the attachment fitting comprises a protrusion configured to be received within a recess in the end plate.

23. The device of any one of examples 21-22 wherein the end plate is slidable over the attachment fitting.

24. The device of any one of examples 21-23 wherein, when the attachment fitting and the end plate are mated together, the longitudinal plate converges towards the stem as it extends away from the end plate.

25. The device of any one of examples 21-24 wherein, when the attachment fitting and the end plate are mated together, the longitudinal plate extends further in a longitudinal direction than the stem.

26. The device of any one of examples 21-25 wherein the end plate comprises a first hole and the attachment fitting comprises a second hole configured such that when the attachment fitting and the end plate are mated together, the first hole and the second hole are substantially aligned.

27. The device of example 26, further comprising a second fastener configured to be inserted into both the first hole and the second hole to secure the attachment fitting and the end plate together.

28. The device of any one of examples 21-27, further comprising:
first and second holes in the longitudinal plate;
third and fourth holes in the stem, wherein, when the device is installed, the first fastener extends through the first and third holes; and
a second fastener coupling the longitudinal plate to the stem, wherein the second fastener is configured to extend through the second and fourth holes.

29. The device of example 28, further comprising a fifth hole in the longitudinal plate; and a third fastener configured to extend through the fifth hole and into the first bone without passing through the stem.

30. The device of any one of examples 21-29 wherein the stem is tiered such that a first portion of the stem nearest to the attachment fitting has a larger cross-sectional dimension than a second portion of the stem.

31. A device for use during an arthroplasty procedure of a joint of a patient, the joint extending between a first joint end of a first bone and an abutting second joint end of a second bone of the patient, the device comprising:
a first component comprising:
an end plate;
a longitudinal plate extending from the end plate and configured to be disposed along a medial, longitudinal surface of the first bone, the longitudinal plate having a hole formed therein;
a second component comprising:
a stem configured to extend along an intra-medullary canal of the first bone, the stem having a second hole formed therein; and
an attachment fitting coupled to a first end of the stem and configured to be positioned at the first joint end of the first bone when the stem is disposed within the intra-medullary canal of the first bone,
wherein the first component and the second component are moveable between an uncoupled configuration and a coupled configuration, and wherein in the coupled configuration the first hole of the longitudinal plate and the second hole of the stem are substantially aligned.

32. The device of example 31, further comprising a fastener for coupling the longitudinal plate to the first bone, and wherein, when the device is installed, the fastener extends through the first hole and the second hole, passing at least partially through the longitudinal surface of the first bone.

33. The device of any one of examples 31-32 wherein:
the joint is a metatarsophalangeal joint;
the first bone is a metatarsus bone;
the second bone is an abutting proximal phalanx bone; and
the end plate is convex.

34. The device of any one of examples 31-32 wherein:
the joint is a metatarsophalangeal joint;
the first bone is a proximal phalanx bone of a foot;
the second bone is an abutting metatarsal bone; and
the end plate is concave.

35. A method of performing an arthroplasty procedure on a joint of a human patient, the joint extending between a first joint end of a first bone and an abutting second joint end of a second bone of the patient, the method comprising:
removing a portion of the first joint end of the first bone;
coupling a first component of an implant to the first joint end of the first bone, such that—
a stem of the first component is disposed within an intra-medullary canal of the first bone; and
an attachment fitting coupled to a first end of the stem is positioned at the first joint end of the first bone;
coupling a second component of the implant to the first component, such that—
an end plate of the second component is mated with the attachment fitting and disposed over the first joint end of the first bone; and
a longitudinal plate extends from the end plate along a medial, longitudinal surface of the first bone; and
extending a fastener between the longitudinal plate and the stem, the fastener passing through the longitudinal surface of the first bone.

36. The method of example 35 wherein coupling the second component of the implant to the first component comprises slidably mating the end plate of the second component to the attachment fitting of the first component.

37. The method of example 36 wherein coupling the second component of the implant to the first component further comprises extending a second fastener through the end plate and the attachment fitting.

38. The method of any one of examples 35-37 wherein the joint is a metatarsophalangeal joint, the first bone is a metatarsus bone, and the second bone is an abutting proximal phalanx bone.

39. The method of any one of examples 35-37 wherein the joint is a metatarsophalangeal joint, the first bone is a proximal phalanx bone of a foot, and the second bone is an abutting metatarsal bone.

40. The method of any one of examples 35-39, further comprising:
drilling a hole through at least a portion of the first bone prior to extending the fastener; and
passing the fastener through the hole.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for use during an arthroplasty procedure of a metatarsophalangeal joint of a patient, the joint extending between a first joint end of a first bone and an abutting second joint end of a second bone of the patient, the device comprising:
a first component including—
an attachment fitting configured for disposing over the first joint end of the first bone; and
a stem extending from the attachment fitting and sized and configured for extending along an intra-medullary canal of the first bone, the stem comprising first and second holes;
a second component including—
an end plate configured to slidably mate with the attachment fitting; and
a longitudinal plate extending from the end plate and configured for disposing along a medial, longitudinal surface of the first bone, the longitudinal plate comprising third, fourth, and fifth holes; and
at least one fastener for coupling the longitudinal plate to the first bone and to the stem;
wherein the attachment fitting comprises a protrusion configured to be received within a recess in the end plate;
wherein the end plate has a shape corresponding to a natural shape of an end portion of a metatarsus bone or a proximal phalanx bone of a foot of the patient;
wherein, when the attachment fitting and the end plate are mated together:
the longitudinal plate extends further in a longitudinal direction than the stem and converges towards the stem as it extends away from the end plate,
the at least one fastener extends through the third and first holes.

2. The device of claim 1 wherein the end plate is slidable over the attachment fitting.

3. The device of claim 1, wherein, when the attachment fitting and the end plate are mated together, the first hole and the third hole are substantially aligned.

4. The device of claim 3, wherein the at least one fastener comprises a first fastener, and wherein the device further comprises a second fastener configured to be inserted into both the fourth hole and the second hole to secure the attachment fitting and the end plate together.

5. The device of claim 4, further comprising a third fastener configured to extend through the fifth hole and into the first bone without passing through the stem.

6. The device of claim 1, wherein the stem is tiered such that a first portion of the stem nearest to the attachment fitting has a larger cross-sectional dimension than a second portion of the stem.

7. The device of claim 1, wherein:
the first bone is a metatarsus bone;
the second bone is an abutting proximal phalanx bone; and
the end plate is convex.

8. The device of claim 1, wherein:
the first bone is a proximal phalanx bone of a foot;
the second bone is an abutting metatarsal bone; and
the end plate is concave.

* * * * *